(12) United States Patent
Xu et al.

(10) Patent No.: US 7,345,030 B2
(45) Date of Patent: Mar. 18, 2008

(54) USE OF N-ACETYL-D-AMINOGLYCOSAMINE IN TREATMENT OF ORGAN LESIONS RELATED TO TOXICOSIS OF DRUGS OR CHEMICALS

(75) Inventors: Qiwang Xu, Chongqing (CN); Junkang Liu, Chongqing (CN); Zetao Yuan, Chongqing (CN)

(73) Assignees: Third Military Medical University, Chinese People's Liberation Army, P.R. of China, Chongqing (CN); Bio-Wave Institute of Suzhou Hi-Tech New District Corporation, Ltd., Jiangsu (CN); Beijing Sino-Hongkong Dafu Science & Technology of Biowave Co., Ltd., Beijing (CN)

( * ) Notice: Subject to any disclaimer, the term of this patent is extended or adjusted under 35 U.S.C. 154(b) by 0 days.

(21) Appl. No.: 10/551,091

(22) PCT Filed: Mar. 29, 2004

(86) PCT No.: PCT/CN2004/000276

§ 371 (c)(1),
(2), (4) Date: Jul. 25, 2006

(87) PCT Pub. No.: WO2004/084914

PCT Pub. Date: Oct. 7, 2004

(65) Prior Publication Data

US 2006/0281707 A1    Dec. 14, 2006

(30) Foreign Application Priority Data

Mar. 27, 2003 (CN) ............................. 03 1 08279

(51) Int. Cl.
*A61K 31/70*    (2006.01)
*C07H 5/04*    (2006.01)

(52) U.S. Cl. ........................................ 514/62; 536/55.2
(58) Field of Classification Search .................. 514/62; 536/55.2

See application file for complete search history.

(56) References Cited

U.S. PATENT DOCUMENTS

| 5,116,615 A | 5/1992 | Gokcen et al. |
| 5,217,962 A | 6/1993 | Burton et al. |

FOREIGN PATENT DOCUMENTS

| EP | 0 372 730 B1 | 6/1990 |
| JP | 59-13708 | 1/1984 |
| JP | 2 11505 | 1/1990 |
| JP | 10-287570 | 10/1998 |
| WO | WO 91/02530 | 3/1991 |
| WO | WO 97/18790 | 5/1997 |
| WO | WO 99/53929 | 10/1999 |

OTHER PUBLICATIONS

O'Neil et al. (eds., I), The Merck Manual, 13th Edition, Merck & Co., Whitehouse Station, NJ, 2001, see entry No. 3246, only p. 567 supplied.*
O'Neil et al. (eds., II), The Merck Manual, 13th Edition, Merck & Co., Whitehouse Station, NJ, 2001, see entry No. 4471, only pp. 793-794 supplied.*

* cited by examiner

*Primary Examiner*—L. E. Crane
(74) *Attorney, Agent, or Firm*—Antonelli, Terry, Stout & Kraus, LLP.

(57) ABSTRACT

The present invention is directed to the use of N-acetyl-D-glucosamine to treat organ lesions caused by toxicants and drugs. The present invention is also directed to a method for treating organ lesions caused by toxicant comprising administering to a patient suffering from organ lesions a pharmaceutical composition comprising N-acetyl-D-glucosamine or a pharmaceutically acceptable salt thereof.

3 Claims, No Drawings

USE OF N-ACETYL-D-AMINOGLYCOSAMINE IN TREATMENT OF ORGAN LESIONS RELATED TO TOXICOSIS OF DRUGS OR CHEMICALS

This application is the national stage application filed under 35 U.S.C.§371 of PCT International Application No. PCT/CN04/00276 filed on Mar. 29, 2004, and which claims priority from the Chinese Patent Document No. 03108279.3, filed Mar. 27, 2003.

TECHNICAL FIELD

The present invention relates to the use of N-acetyl-D-glucosamine or pharmaceutically acceptable salts thereof for in treating organ lesions caused by toxicosis of drugs or toxicants, and the use of N-acetyl-D-glucosamine or pharmaceutically acceptable salts thereof in the manufacture of a medicament for treating organ lesions caused by toxicosis of drugs or toxicants.

BACKGROUND ART

Many researches are directed to organ lesions caused by various toxicants and drugs. In daily life, various toxicants mainly enter into human body via respiratory tract, skin and digestive tract, and result in multi-system and organ lesions. There are many injury mechanisms. In lead poisoning, lead as a poly-affinity toxicant acts on all systems of body, and mainly injures nerve system, hematopoietic system, digestive system and cardiovascular system, wherein the most important injury is the metabolism disorder of porphyrin, an intermediate product during the synthesis of hemoglobin. In mercury poisoning, mercury ion binds to mercapto groups of enzymes in vivo, and thus inhibits the activity of enzymes and blocks the normal metabolism of cells, which further cause central nerve and autonomic nerve dysfunctions of central nerve and autonomic nerve and lesions of digestive tract and kidney. In poisoning of arsenic and compounds thereof, arsenic and oxides thereof bind to mercapto groups of cellular enzymes in vivo, in particular, they bind to the mercapto group of pyruvate oxidase and inactivate this enzyme, which affect normal metabolism of cells and firstly result in lesions of nerve system and blood capillary, so that human body exhibits toxic symptoms. In methanol poisoning, methanol mainly acts on central nerve system and brings about a selective toxic effect, and the toxic symptoms are similar to alcoholism but more serious. Methanol destroys intracellular oxidization, so that the accumulation of lactic acid and other organic acids causes acid poisoning. Cyanide poisoning causes oxidization disorder in body, which results in so-called "intracellular choke". Although there are various toxicosis mechanisms, most of them relate to effects of cellular level on redox reactions during the metabolism process, or effects that toxicants act directly as oxidants, or effects that toxicants destroy activity of enzymes.

In drug poisoning, barbiturate poisoning mainly results in the inhibition of central nerve system, the most prominent toxic effect of chloropromazine is extrapyramidal motor system dysfunction which exhibits muscle convulsion, akathisia, etc. These symptoms cannot be healed for a long time after drug withdrawal.

At present, therapeutics for treating toxicosis of drugs and toxicants include: intravenous injection of 10% calcium gluconate, 1-2 times per day, for 2-3 days, deleading therapy with sodium dimercaptosuccinate, de-arsenicing therapy with dimercaptopropanol, or gastrolavage; gastrolavage with sodium hydrogen carbonate or peritoneal dialysis for treating methanol poisoning; therapy for treating cyanide poisoning by using sodium thiosulfate, or glucose, or dicobalt edetate in combination with glucose. In general, said therapeutics are at the level of competitive binding, quick dilution, concentration decrease and damage reduction, and there is essentially not therapeutics that has said functions and can act against toxicants and drugs at sites of toxic action in order to eliminate the toxic effect fundamentally.

N-acetyl-D-glucosamine is a chemical reagent. From the 1990's, it is continually used to treat diseases such as pericementitis (WO9102530A1), microbiological infection (WO9718790A3), intestinal inflammation (WO9953929A1), cornea disease (JP10287570A2), hypertrophy of the prostate (U.S. Pat. No. 5,116,615), and so on. It is also applied in cosmetology (JP59013708A2), shampoo preparation (JP2011505A2), and the like, but it has not been used in the manufacture of a medicament for treating organ lesions caused by toxicosis of drugs or toxicants.

The inventor of the present invention finds that N-acetyl-D-glucosamine and pharmaceutically acceptable salts can rapidly and effectively treat toxic reactions of drugs and toxicants, competitively bind to toxicants to convert toxicants into nontoxic substances, reduce oxidation-type toxicants to alleviate their toxic effects on cell components, and form a dynamically changed isogeneric action barrier on surface of cells and bio-macromolecules to eliminate and segregate toxic effects, thereby the present invention is carried out.

CONTENTS OF THE INVENTION

One object of the present invention is to provide a use of N-acetyl-D-glucosamine or pharmaceutically acceptable salts thereof in the treatment of organ lesions caused by toxicosis of drugs or toxicants.

Another object of the present invention is to provide a use of N-acetyl-D-glucosamine or pharmaceutically acceptable salts thereof in the manufacture of a medicament for the treatment of organ lesions caused by toxicosis of drugs or toxicants.

Another object of the present invention is to provide a method for treating organ lesions caused by toxicosis of drugs or toxicants, comprising administering a patient a pharmaceutical composition comprising an effective amount of N-acetyl-D-glucosamine or pharmaceutically acceptable salts thereof.

The said N-acetyl-D-glucosamine is a compound having a molecular formula of $C_8H_{15}NO_6$ and a structure formula (I).

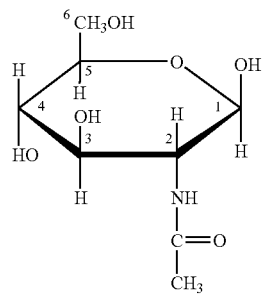

The examples of pharmaceutical acceptable salts of N-acetyl-D-glucosamine that can be used in the present invention include, but are not limited to the salts formed with inorganic acids, such as hydrochloride, hydrobromide, borate, phosphate, sulfate, hydrosulfate and hydrophosphate, and the salts formed with organic acids, such as citrate, benzoate, ascorbate, methylsulfate, picrate, fumarate, maleate, malonate, succinate, tartrate, mesylate, and glucose-1-phosphate.

In the pharmaceutical composition of the present invention, the content of N-acetyl-D-glucosamine or pharmaceutically acceptable salts thereof is generally from 0.1 to 10% by weight.

Besides N-acetyl-D-glucosamine or pharmaceutically acceptable salts thereof, the pharmaceutical composition of the present invention may further comprise excipients or carriers well known in the art. According to the desired administration manner, the person skilled in the art can readily select suitable excipients or carriers.

The pharmaceutical composition of the present invention can be in various dose forms and can be administrated in various manners, for example, intestinal administration such as oral administration, or parenteral administration such as intravenous injection, transdermal injection, etc. Typically, the pharmaceutical composition of the present invention is an injectable dose form, and is administered parenterally. For example, N-acetyl-D-glucosamine or pharmaceutically acceptable salts thereof can be readily dissolved in injectable water or physiological saline to form an injectable dose form.

The pharmaceutical composition of the present invention can be administered in a manner of single dose per day or multidoses per day, such as 3-4 doses per day. The dose of said pharmaceutical composition depends on patient's age, condition, symptom, and administration manner. In general, as to an adult patient having a bodyweight of 75 kg, the dose of said pharmaceutical composition is 1-100000 mg per day, preferably 10-10000 mg per day, based on active component.

Another object of the present invention is to provide a process for manufacturing a pharmaceutical composition for treating organ lesions caused by toxicosis of drugs and toxicants, comprising mixing an therapeutically effective amount of N-acetyl-D-glucosamine or pharmaceutically acceptable salts thereof with excipients or carriers to form a preparation.

Although the inventor does not intend to be restricted by any theory, the inventive point of the present invention is derived from the basic thinking of bio-wave theory. In the research of "bio-wave" theory, the present inventor has set up an organism wave-growth model. Through deeply researching the molecular mechanism of the organism wave-growth, the inventor puts forward a micro-heterology variation mechanism, wherein the change rate of biological wave of organism depends on the change extent of outer environments. After the organism is wounded, the inner environments of said organism changes quickly, which promotes the generation of micro-heterology and disbalance between said organism and environments, and causes local lesions or systematic toxic symptoms. According to molecular biological analysis, these lesions and toxic symptoms relate to the unstability even loss of function of proteins, especially various enzymes under changed conditions, especially changed temperature in the presence of microorganism metabolism products.

The inventor confirms with experiments that N-acetyl-D-glucosamine or pharmaceutically acceptable salts thereof not only make organism cells to reveal a normal bio-wave characteristic, but also cause the wave reveal a finer wave mode. This indicates that these compounds have a function of promoting bio-waves. This wave-promoting function may explain the mechanism of treatment organ lesions caused by toxicants and drugs.

The inventor finds that the supporting effect of N-acetyl-D-glucosamine and the antitoxic ability of binding to oxidation-type toxicants are substantively identical to that of glucose, while N-acetyl-D-glucosamine as a chiral drug has a diphase variation characteristics, which means it can randomly bind to components of organism in an isologous manner of toxic configuration of toxicants to form a segregation area between said toxicants and organism components such as cells or enzymes. As compared to toxicants, N-acetyl-D-glucosamine has a higher affinity to organism components, because N-acetyl-D-glucosamine has a dynamically changeable configuration that can randomly maintain changeable features corresponding to configurations of biomacromolecules. This ability is important in natural protection mechanism of stabilizing structure and function of cells or molecules thereof formed via natural evolution of endogenous substances that are present in vivo for a long-term.

EMBODIMENTS FOR CARRYING OUT THE INVENTION

The beneficial effects of the present invention are further demonstrated by the following examples, but it shall be understood that these examples are merely to illustrate the present invention, rather than to restrict the scope of the present invention in any aspect.

EXAMPLE 1

Promoting Wave Test of the Compound of Formula (I)

1. Experimental Materials and Method:

1.1 Sample: Pure Compound of Formula (I)

1.2 Experimental Materials:
   Strain: *Proteus Mirabilis* that meets the following biochemical reaction characteristics: dynamics (+), urease (+), lactose (−), glucose (+), $H_2S$ (−), phenylalanine deaminase (+).
   Culture medium: modified LB culture medium (components: 1% tryptones, 0.5% yeast extract, 1% sodium chloride, 0.1% glucose, 0.002% TTC, and pH=7.2 to 7.4).

1.3 Experimental Method:
   Control sample: the *Proteus Mirabilis* were inoculated at the center of LB plate, and incubated at 37° C. for 9 hours;
   Test sample: the compound of formula (I) with a final concentration of 0.5% was added to the LB plate, then the *Proteus Mirabilis* were inoculated by the same method, and cultured at 37° C. for 9 hours.

2. Experimental Results and Evaluation:
   The control sample exhibited concentric rings with an interval of 3 hours, which extended outward continually. The test sample showed not only concentric rings with an interval of 3 hours, but also many fine waves on each ring in comparison with the control sample.
   The experiment adopts a bio-wave model to research the promoting wave function of the compound of formula (I). The results showed that the compound of formula (I) was not only able to cause bacterial cell to reveal a normal bio-wave characteristic, but also cause the wave reveal finer wave mode. These indicated that the compound of formula (I) has a function of promoting bio-waves. It is anticipated that this wave-promoting function could treat organ lesions caused by toxicants and drugs.

EXAMPLE 2

Toxicological Test of the Compound of Formula (I)

The toxicological test of the compound of formula (I) includes:
1. Acute toxicity test: including tests of oral administration, intravenous injection administration, and maximum limit amount for administration;
2. Ames test;
3. Micronucleus test of mouse bone marrow cell;
4. Abnormality test of mouse sperm;
5. Aberration test of mouse testis chromosome;
6. Chronic lethal test;
7. Sub-chronic toxicity (feed for 90 days) test;
8. Traditional deformity-inducing test.

The results of these tests showed that in the acute toxicity test of the compound of formula (I), the acute toxicosis reaction had not appeared when the dosage more than 2 g/kg was taken; in the long-period toxicity test, the maximum dosage had reached up to 1 g/kg, and after the treatment and observation for four weeks, there was no intoxication reaction yet; and in the reproduction test, the mice were feed with a routine dosage of 7 mg/kg for 3 generations, it had been proved that the compound of formula (I) had no influence on the pregnancy, birth, nurse, and the growth of baby mice, so that the compound of formula (I) is a substance without toxicity.

EXAMPLE 3

Animal Tests

1. Methanol Poisoning Test

30 Kunming mice were randomly divided into two groups, i.e., 15 mice in test group (I) and 15 mice in test group (II), and another 15 mice were used as control. Each mouse fed with methanol in a dose of 0.2 ml/20 g bodyweight. The mice of the control group were not treated, wherein the mice exhibited delirium, colliding things and blurred vision, 13 mice were blind in both eyes and myasthenia of limbs within about 2 hours, 10 mice sequentially died and 3 mice still were blind. The mice of the test group (I) were intra-peritoneally injected with an aqueous solution of N-acetyl-D-glucosamine having a concentration of 0.1 g/ml in a dose of 0.1 ml/20 g bodyweight, just after they were fed with methanol. The results showed that 8 mice were blind after 2 hours (wherein 5 mice sequentially died), and 2 mice exhibited obvious psychiatric symptoms. The mice of the test group (II) were intra-peritoneally injected with an aqueous solution of N-acetyl-D-glucosamine having a concentration of 0.1 g/ml in a dose of 2 ml/20 g bodyweight, just after they were fed with methanol. The results showed that the mice exhibited better condition, wherein 4 mice exhibited delirium and myasthenia of limbs, no mouse was blind, and 2 mice died within 12 hours.

2. Rogor Poisoning Test

30 Kunming mice were randomly divided into three groups, i.e., 10 mice in control group, 10 mice in test group (I) and 10 mice in test group (II). The mice were orally fed with 10000 times diluted rogor stock solution (commercially obtained from Chongqing Agriculture Chemicals Group, 500 ml/bottle, standard: GB15583-1995) in a dose of 0.5 ml per mouse for consecutive 3 days. The mice of the control group were not treated, and exhibited toxic symptoms of food-intake reduction and dysphoria after they were continuously fed for 3 days, then exhibited diarrhoea, watery stool, blurred vision during action, some mice exhibited symptoms of coma, twitch, urinary and fecal incontinence, etc., and 8 mice died. The mice of the test groups were treated by intra-peritoneal injection of an aqueous solution of N-acetyl-D-glucosamine having a concentration of 5 g/100 ml in a dose of 0.2 ml for the test group (I) and a dose of 2 ml for the test group (II). The results showed that 4 mice died in the test group (I) and 1 mouse died in the test group (II), and the corresponding symptoms were well controlled. The mice of test groups were significantly different from the mice of the control group.

3. Lead Poisoning Test

30 Kunming mice were made as lead poisoning models by a method of feeding litharge. The mice of control group, i.e., model group were not treated, wherein the mice exhibited obvious symptoms of polysialia, emesis, diarrhoea, constipation, twitch, etc., the death rate was 8/10 within 3 days, and the death rate was 10/10 within 7 days. The mice of the test group (I) were treated by intra-peritoneal injection of N-acetyl-D-glucosamine in a dose of 0.2 ml×10% (weight/volume), and the mice of the test group (II) were treated by intra-peritoneal injection with N-acetyl-D-glucosamine in a dose of 2 ml×10% (weight/volume). The death rate of mice was separately 7/10 and 2/10 within 3 days, and the death rate of mice was 1/3 and 0/8 within the following 4 days. The survival mice exhibited better conditions. N-acetyl-D-glucosamine showed obviously function of treating reaction of lead poisoning, controlling relevant symptoms, and reducing death rate.

According to the above examples, N-acetyl-D-glucosamine can effectively eliminate toxic effects of at least toxicants such as metal ions, organophosphorus pesticides, methanol, etc. that have different action mechanisms.

The compound of the formula (I) of the present invention not only has certain effect, but also does not exhibit side-effect as conventional antidotes. Hence, it is a promising drug.

What is claimed is:

1. A method for treating organ lesions caused by a toxicant selected from the group consisting of methanol, organophosphorus pesticides and metal ion sources, comprising administering to a patient suffered from the organ lesions a pharmaceutical composition comprising N-acetyl-D-glucosamine or pharmaceutically acceptable salts thereof as well as a pharmaceutically acceptable carrier.

2. A method according to claim 1, wherein said pharmaceutical composition is in an injectable form and is parenterally administered.

3. A method according to claim 1, wherein the N-acetyl-D glucosamine or the pharmaceutically acceptable salts thereof in said pharmaceutical composition has a concentration of 0.1-10% by weight.

* * * * *